United States Patent [19]

Wrasidlo

[11] Patent Number: 5,166,319
[45] Date of Patent: Nov. 24, 1992

[54] INTERFACIAL CONDENSATION OF BIOACTIVE COMPOUNDS AND THE SITE-SPECIFIC COMPOUNDS AND CONJUGATES THEREOF

[75] Inventor: Wolfgang J. Wrasidlo, La Jolla, Calif.

[73] Assignee: Brunswick Corporation, Skokie, Ill.

[21] Appl. No.: 419,337

[22] Filed: Oct. 10, 1989

[51] Int. Cl.$^5$ ............... C07K 15/28; C07K 17/02
[52] U.S. Cl. .............. 530/391.1; 530/391.3; 530/391.5; 530/391.7; 530/391.9; 530/405; 530/406; 530/409; 530/410; 435/188; 424/450; 536/27; 534/15; 552/588; 552/262
[58] Field of Search ............... 530/388, 389, 391, 405, 530/406, 409, 410, 391.1, 391.3, 391.5, 391.7, 391.9; 435/188, 235.1; 424/450; 536/27; 534/15; 552/588, 625

[56] References Cited

U.S. PATENT DOCUMENTS

| | | | |
|---|---|---|---|
| 3,959,079 | 5/1976 | Mareschi et al. | 195/63 |
| 4,066,504 | 1/1978 | Krasnobajew et al. | 530/364 |
| 4,522,750 | 6/1985 | Ades et al. | 530/380 |
| 4,671,958 | 6/1989 | Redwell et al. | 424/85.91 |
| 4,699,784 | 10/1987 | Shih et al. | 424/85.91 |
| 4,775,714 | 10/1988 | Hermann et al. | 525/54.1 |
| 4,843,147 | 6/1989 | Levy et al. | 530/391 |
| 4,883,864 | 11/1989 | Scholz | 530/402 |

OTHER PUBLICATIONS

Blair et al. (1983), J. Immunol. Methods 59:129-143.
Lowell et al. (1988), J. Expt. Medicine 167:658-663.

*Primary Examiner*—Christine M. Nucker
*Assistant Examiner*—Kay K. Kim
*Attorney, Agent, or Firm*—Waldron & Associates

[57] ABSTRACT

This invention provides a method of preparing conjugates of bioactive compounds and site-specific compounds in which covalent bonding between the compounds is effected by interfacial condensation while protecting the active binding sites from the condensation reaction. This provides very high yields of the bioactive, site-specific conjugate, the products are homogeneous and it provides novel conjugate products. It is of particular advantage for monoclonal antibodies conjugated with cytotoxic agents.

23 Claims, No Drawings

INTERFACIAL CONDENSATION OF BIOACTIVE COMPOUNDS AND THE SITE-SPECIFIC COMPOUNDS AND CONJUGATES THEREOF

FIELD OF INVENTION

The technical field of the present application relates to conjugates of bioactive compounds and site-specific compounds in which covalent bonding between the compounds is effected by interfacial condensation while protecting the active binding sites from the condensation reaction.

The technical field also relates to the formation of conjugates of bioactive compounds and site-specific compounds. The compounds forming the conjugates may be linked together directly or via various linker molecules.

More specifically, it relates to therapeutic preparations of monoclonal antibodies conjugated with cytotoxic agents via interfacial condensation reactions.

BACKGROUND OF THE INVENTION

The present invention relates to a method of making covalently bound conjugates of bioactive compounds with biologically site-specific compounds. The bioactive compounds are cosmetic, treatment or therapeutic compounds, such as drugs, hormones, cytotoxic compounds, and the like; the site-specific compounds are desirably antibodies, and particularly monoclonal antibodies and the like. The conjugates from this method retain the bioactive and site-specific properties of the reactants.

It also relates to the chemical compounds which are the product of such methods, and particularly to compounds which are covalently bound conjugates of bioactive molecules and site-specific proteins. In very particular terms it relates to highly homogeneous conjugates with high levels of bioactive action and site specificity and a minimum of side effects and systemic effects in host organisms when administered.

This invention also relates to the method of treating a host organism with such conjugates for the purposes of medical care or serious cosmetic needs of the individual.

In medical treatment of patients, a paramount problem is that powerful prospective drugs can not be used because their side effects on the rest of the body of the patient are too damaging. A great number of chemical compounds, both natural and synthetic, show initial promise as possible new drugs for a wide variety of diseases. Frequently, initial screening tests of a chemical will show good toxicity, growth regulatory effects, immune stimulation or suppression, or other indications of useful properties in vitro. However, when tests are conducted on living organisms, the latent benefit of a large majority of these potential drugs is never realized or severely limited by side effects manifested in vivo. Often, the problem is one of dosage. The required amount or dose of the drug which exhibits the desired therapeutic effect is too high to be tolerated by the organism being treated. This is particularly evident in chemotherapy for cancer in man and other animals. Severe side effects generally accompany the anticancer treatment. Many drugs with even stronger anticancer activity than those presently in use are available, but under normal cytotoxic use regimens, the use of these drugs would kill the patient faster than the cancer.

Many approaches have been tried to circumvent the toxicity problem of strong drugs. The most attractive among these involves the use of chemical conjugates as a means of targeting the drug specifically to the site of action. The goal is to form a conjugate by reacting a drug with a site-specific compound and to use the conjugate for its combination of therapeutic and site-specific properties. The result of effective specific targeting is that it would allow a small dose of conjugate to create a high concentration of the drug in the cancer cells, parasitic organisms, or secretory cells, for example, while keeping the general body burden low. Targeting means which have shown some initial success, and which probably have the greatest potential, are biologically site-specific proteins, especially the monoclonal antibodies and antibody fragments. In their original state, these will bind to particular antigens. The potential advantages of conjugates containing selected monoclonal antibodies and an illustration of the therapeutic effect of these conjugates on cancer cells are described in articles by Yang, H. M. and Reisfeld, R. A., Proc. Natl. Acad. Sci. USA, vol. 85, pps. 1189–1193, February, 1988. and Yang, H. M. and Reisfeld, R. A., J. National Cancer Institute, Vol. 80, No. 14, pps. 154–159, September, 1988.

When prepared by proper screening techniques, monoclonal antibodies possess exquisite specificity for their targets. A target of great medical importance is solid human tumor antigen; these tumors are very resistant to treatment with chemotherapeutic drugs. There are several monoclonal antibodies that are known to be site-specific for these tumors.

The major problems in attempts to achieve therapeutic and site-specific drug compositions arise from the preparation of the drug-antibody conjugate. Traditional chemical methods to prepare conjugates by attaching drugs and related materials to antibodies, either directly or via a linker molecule, suffer from four main problems: namely, that the linkage reaction occurs randomly on active groups of the antibody molecule, frequently with active groups that are near or in the site-specific regions of the molecule, resulting in seriously altered or reduced specificity in the conjugate; the linkage is ordinarily partially labile under physiological conditions, resulting in hydrolysis which causes at least some systemic release of the drug before it reaches its target; the ratio of reagents and the stoichiometry of reagents for control of the conjugation reaction is very difficult to achieve in aqueous solutions since most activating agents that are used for the drugs are degraded by water; and, lipophilic drugs are very difficult, or impossible to link to antibodies to form homogeneous conjugates.

The biologically site-specific compound depends upon the presence of one or more active binding sites in its molecule for the crucial ability to bind only with its target antigen. This is best exemplified by antibodies. It can be seen that the traditional methods for conjugating therapeutic compounds to antibodies show selectivity only in respect to reacting with particular reactive groups on the amino acids which make up the antibody, the $\epsilon$-amino group of lysine for example, but no specificity regarding the location of the amino acid in the antibody structure. Since the amino acids are distributed in a near random manner within the antibody structure, the conjugation reactions will proceed with reactive groups that are found within the active binding site of the variable regions as well as those in the constant regions of the molecule. Antibody conjugate preparations generated by traditional methods contain a proportion of molecules which have been inactivated or have had their specificity altered because of bioactive compounds conjugated to the antibody within the active binding site. The percentage of antibody molecules with reduced ability to bind the desired target is related to the number and location of reactive groups within the binding site and the reaction conditions employed. If, for example, a single reactive group within the binding site of the antibody was positioned such that a drug conjugated to the antibody through that reactive group prevented all binding to the target antigen, then exhaustive conjugation of an antibody solution could occur and yet result in a preparation with no target specificity. The inevitable result if no adjustments are made is a preparation with reduced specific activity and increased general toxicity. European Patent Application 0 175 617, J. W. Goers et al. describes the problems which have been encountered in this field by reason of loss of site-specificity in the antibody during the reactions with therapeutic compounds. Similar problems in the preparation of platinum based chemotherapeutics are discussed in European Patent Applications nos. 0 167 310 and 0 169 645 by J. G. Hefferman.

The present invention solves each of the four problems mentioned above to yield compositions of bioactive agent-antibody conjugates which are more stable, more homogeneous, more specific than conjugates prepared by other means, have greater specific activity toward target cells, have fewer by-products and which give fewer side-reactions and thus have lower toxicity toward the patient.

The present invention includes conjugates of antibodies, and particularly monoclonal antibodies with bioactive compounds. These conjugates exhibit or provide the bioactivity of the one parent compound and the site-specificity of the other parent compound. The term bioactive compound is employed herein to include cosmetic compounds and therapeutic compounds such as pharmaceuticals, toxins, cytotoxins, alkylating agents, enzymes, antibiotics, antimetabolites, hormones, neurotransmitters, radioopaque dyes, radioactive isotopes, fluorogenics, bio-markers, lectins, photochemicals, cell membrane modifiers, antiproliferatives and heavy metals. These compounds are used for cosmetic and therapeutic purposes and are typically drugs, particularly cytotoxic and cytoactive compounds and substances including radionuclides, diagnostics, such as radiotracers, fluorescing compounds, and the like, hormones, weight gain and weight loss compounds and other bioactive proteins and related biologically produced compounds and the like which are not themselves site specific in their action. In terms of cellular or host organism effect, the bioactive compound is an agent adapted for functions such as cell destruction, prevention of cell proliferation, hormone therapy, gene therapy, diagnosis of cell condition, tracing of cell location, identification of cellular masses, treatment of healthy cells and modification of healthy cells.

Among the applications for the bioactive, site-specific conjugates which utilize the functions described above are: cancer therapy, treatment of rubella, gram negative infections, hepatitis B, blood clots, tetanus, cold infections, rheumatoid arthritis, cardiovascular disease and septic shock. They can also be used in preventing transplant rejection, for renin inhibition, as pro-drugs, non-therapeutic diagnostics and metal ligating compounds.

The term biologically site-specific compound is employed herein to include proteins, antibodies, antibody fragments, liposomes, viruses, phages and steroid hormones. These compounds are typically water soluble or water dispersible and have at least one active binding site that will attach to individual and particular antigens. The antigen will be uniquely characteristic, or nearly so, of the cell or cellular organism to which the therapeutic treatment or bioactive function is directed. It is to be understood that the site-specific compound will have suitable functional groups for forming covalent bonds with the bioactive compound and that these covalent bonds will be located at a location designated as the conjugation site of the site-specific compound. In addition, the active binding site will refer to those locations where the site-specific compound binds to its target molecule or antigen.

The term bioactive, site-specific conjugate is used herein to refer to the product of condensation between the bioactive compound and the site-specific compound and which conjugate exhibits itself or by controlled hydrolysis provides the bioactivity and site-specificity of the parent compounds. At a molecular level there is at least one covalent bond between the two parent compounds which is formed during the condensation reaction. The conjugate may have a stoichiometry such that the ratio of bioactive compound to site-specific compound is less than one. Typically, there will be two or more moles of bioactive compound per mole of site-specific compound.

A particularly important class of bioactive compounds are the powerful cytotoxic and cytoactive compounds which have been excluded from serious investigation and application in the context of conjugates with monoclonal antibodies and other proteins because these compounds are highly lipophilic, soluble in body fat and insoluble in water. There are a substantial number of such compounds of interest, but efforts to conjugate them with monoclonal antibodies and the like have generally resulted in irreversible denaturation of the proteins in the attempt so that the conjugate has no site-specificity. Typical and representative of these compounds are the carotenoids and retinoids.

Carotenoids and retinoids are closely related compounds which are found in a variety of chemical derivatives in most life forms, including humans. Though their natural functions are poorly understood, these families of chemical compounds, particularly the retinoids, have been shown to have effects relating to cellular differentiation. A variety of retinoids have been shown to stimulate neoplastic cells of various types to differentiate into a nonproliferative form. Most experimental evidence is from in vitro systems. Investigations on animals and humans and development of the retinoids and carotenoids as drugs has been hindered by the toxicity of the compounds at efficacious concentrations. Topical applications of various retinoid preparations have been clearly shown to reverse malignant and premalignant skin lesions. The preponderance of data seem to indicate that carotenoids and retinoids have great potential as anticancer agents, at least for cancers of ectodermal origin, and perhaps more diverse pharmacological applications. The primary problems appear to be that specific effects are difficult to ascertain clinically, and retinoids (and perhaps derivatized carotenoids) are toxic at blood levels sufficient to elicit a positive result. Without a method of effectively targeting these molecules in the form of conjugates, they will remain limited to dietary supplements of ill defined effect and topical agents of very limited use.

Because of the very strong lipophilic properties of the retinoids and carotenoids, it has been virtually impossible to carry out chemical reactions that would successfully link them to monoclonal antibodies or other proteins and produce therapeutic, site-specific conjugates containing the retinoid or carotenoid. Using the novel techniques of the present invention for attaching bioactive compounds to antibodies it is possible to make novel retinoid-antibody conjugates. These conjugates can be prepared by attaching the compound directly to the antibody or by inserting a linker molecule between the two. The linkage between the retinoid and either the linker molecule or the antibody can be either labile or not, depending on what is desired for a particular investigation or other therapeutic purpose. Carotenoid-antibody compounds can be prepared in the same manner and will provide a way to investigate and apply the effects of these compounds and their derivatives.

Antibodies, both poly and monoclonal, are highly preferred compounds for site-specific targeting vehicles in conjugates. Their high specificity of target, recent advances in their mass production, and their documented efficacious use against cancers in various experimental and clinical tests would make them the targeting method of choice. Specifically targeting carotenoids and retinoids at cancer cells would create high concentrations at the target sites without concomitant high blood serum levels and risk of systemic effects. Actual effects of site-specific conjugates of retinoids and carotenoids on the target cancer cells could be ascertained without interference from the liver's regulatory mechanism and subsequent toxicity. New derivatives of the retinoids and carotenoids can be prepared and examined for improved therapeutic effect and new types of cancers can be targeted for site-specific, therapeutic attack. The problem is that conventional methods for conjugating antibodies to drugs do not work for the carotenoids or retinoids. These molecules are very insoluble in aqueous solutions, while antibodies are easily denatured in organic solutions.

The present invention includes the discovery that multiphase reaction systems with interfacial condensation can produce a therapeutic and site-specific conjugate from cytotoxic, and particularly lipophilic cytotoxic compounds, typified by carotenoid and retinoid compounds, and antibodies. The production of these conjugates is made possible by the techniques described herein. It also includes the discovery that this is a process for preparation of bioactive, site-specific conjugates which is highly efficient and improves the yield of the desired conjugate products while simplifying the purifications used to make the compositions pharmaceutically acceptable. It has the advantage that it reduces the formation of by-products and the occurrence of side reactions which have attended and seriously compromised other attempts to prepare successful therapeutic, site-specific conjugates. It provides a substantial improvement in the homogeneity of the desired bioactive, site-specific conjugates. For these reasons, the products of the process will have fewer side effects when used in therapeutic treatment of target cells. And, the natural body response to chemical modifications will be substantially less because of the improved homogeneity of the products. Thus, not only can new and improved bioactive, site-specific conjugates be obtained but also there is a significant improvement in the processes for the preparation of bioactive, site-specific conjugates in general.

It is an object of the present invention to provide a method of conjugating biologically site-specific compounds with bioactive compounds to form covalent bonds between them by the use of interfacial condensation reactions.

It is another object of the present invention to provide a method of conjugating biologically site-specific compounds with bioactive compounds in such a way that the active binding site of the site-specific compound is protected and this active binding property is exhibited by the conjugate along with the bioactive effect.

It is a further object of the present invention to provide a method of conjugating biologically site-specific compounds with bioactive compounds which employs interfacial condensation and where the physical phases for the respective compounds are selected to maximize a chemically favorable environment for each compound.

It is yet another object of the present invention to provide a method of conjugating biologically site-specific compounds with bioactive compounds in which the covalent bonding between the compounds can include a group adapted to provide selected atomic spacing between the compounds or preferential reaction sites for covalent bonding on the compounds and optionally a physiologically cleavable group adapted to release the bioactive compound at the selected site of the target antigen.

It is an object of the present invention to provide a method for preparing bioactive, site-specific conjugates by interfacial condensation in which the bioactive compound is modified by reaction with a spacing or linking or physiologically cleavable group prior to condensation with the biologically site-specific compound.

Another object is the provision of the bioactive, site-specific conjugates which are the products of the processes of the present invention.

Yet another object is the provision of bioactive, site-specific conjugates of bioactive compounds with proteins, particularly with antibodies, and still more particularly with monoclonal antibodies.

Still another object is the covalently bound bioactive, site-specific conjugates of lipophilic bioactive compounds and monoclonal antibodies and other proteins.

A further object is the treatment of host organisms with the conjugates of the present invention.

SUMMARY OF THE INVENTION

In summary form, this invention is the preparation of bioactive, site-specific conjugates using interfacial condensation to form a covalent or ionic bond between a bioactive compound and a biologically site-specific compound while protecting the active binding site from the condensation reaction and recovering the conjugate product. It also includes the products and bioactive uses of such products. Through this method the conjugate has the site-specific and bioactive properties of the individual reactants. In a great number of potential applications this invention may also orient the molecules for reaction, and will prevent inactivation of activating compounds, conjugate intermediates, and the drug or other bioactive molecule to be attached. The interfacial condensation can employ any multiphase system in which the individual compounds are in separate phases and react at or near the interface between the phases.

Usually, two phases will be used; these include, but are not limited to, solid-liquid systems, liquid-gas systems and organic-aqueous systems. The specific physical-phases and reagents used in a particular system are determined by the physical properties and the chemistry of the bioactive compound which is to be linked to the site-specific compound and the type of linkage which is desired.

The practical benefits which accrue from the use of this novel approach to conjugating bioactive molecules to site-specific compounds, such as antibodies are that the covalent linkage does not attach to the active binding sites of the antibody, thus preserving the specific site activity of the conjugate and reducing nonspecific toxicity; the linkage of the drug (for example) to the antibody is more uniform and more stable; site-specific compound, bioactive compound, linking, spacing or cleavable groups, and conjugates are always in the proper orientation at the site of reaction in the interface between compatible solvents in their separate phases, so denaturation of the site-specific regions in the compounds or conjugate is not a problem; and virtually all types of molecules, including those which are very lipophilic, can be conjugated to site-specific compounds, and without deleterious solvent effects on either constituent.

This invention achieves these benefits by conducting the processes under conditions that take best advantage of the diverse chemistries of the biologically site-specific compounds and the bioactive compounds to be conjugated, the parameters of the conjugation reaction, and the geometry and structure of the active binding sites.

DETAILED DESCRIPTION OF THE INVENTION

This invention will now be described in terms of the detailed application of its principles and by reference to its illustrative examples. Interfacial condensation is a method of reacting chemical compounds in which there are immiscible bulk phases, each of the phases contains a reactant; the reactants are present at the interface and the reaction occurs in the region of the interface. Its best known industrial application is the polymerization to form nylon. The bulk phases of this invention will usually be a liquid aqueous phase for the site-specific compound and a solid, liquid organic or gas phase for the bioactive compound.

The active binding sites in biologically site-specific compounds such as antibodies have unique, antigen specific structures characterized by both amino acid sequences and steric parameters which define a highly unique shape. The steric parameters are generally characterized by the presence of a portion of the molecule in which there is a fold or "recess" in the molecular surface. The remainder of the protein chain has a rather loose and variable geometric orientation. As long as the active binding site retains its steric configuration and its amino acid sequences, the molecule can recognize and bind to the antigen for which it is configured. There already exist a very substantial number of particular antibody-antigen combinations which are well known and are published.

In terms of chemical reactivity, the amino acids of the sequences in both the region of the fold and in the loose and variable regions of the molecule will be capable of reacting with the bioactive compound. During the condensation reactions, the amino acids in both regions are susceptible to forming the covalent bonds with the bioactive compound. The reaction conditions of this invention will protect the amino acid sequences of the active binding sites while the covalent bonding reactions occur with the other amino acid sequences.

This invention utilizes interfacial condensation reactions and requires that the bioactive compound is contained in a structure or phase that is immiscible with the site-specific compound. Interfacial condensation reactions, in general, involve reactants in at least two immiscible phases. The condensation reaction between the reactants occurs at the interface between the phases. It is therefore preferred that as much interface as possible exist between the phases. For this reason it is common in a two phase system to have one phase (the dispersed phase) dispersed throughout the other (the continuous phases). The dispersed phase is generally found in the form of droplets, small solid particles, or bubbles distributed throughout the continuous phase. However, if the droplets, particles, or bubbles of the dispersed phase become too small, then a solution results and the biphasic nature of the reactants disappears. For this reason, the size of these droplets, particles, or bubbles is limited by definition because they must remain immiscible thereby forming an interface with the continuous phase.

The foregoing is an important aspect of the present invention. Each specific antibody will have its own unique characteristics and properties, but, in most cases, the fold in the conformation of the active binding site will fall within a range of dimensions so that any structure, e.g. an immiscible droplet or crystallite of bioactive compound reagent, having a local radius of curvature of from about 10, preferably about 20 Angstroms and greater will be unable to penetrate the fold to interact with the reactive amino acid sequences that are in or near the fold. During the interfacial condensation, the conditions of the respective immiscible phases are maintained to protect the active binding site from the condensation reaction. This is accomplished because by definition the dispersed phase must be of a size which will enable the two phases to remain immiscible. Droplets, particles, or bubbles which might fit into the active binding site will not tend to form because at that size the phases tend to lose their immiscibility. The reaction interface is therefore physically excluded from the active binding site because the immiscible droplets, particles, or bubbles containing the bioactive compound are too large to fit into the active binding site. By protecting the active binding site in this manner, the bioactive reagents can therefore be caused to react with the other amino acid sequences in the loose and variable regions of the protein molecule. Therefore, the conjugation site or sites between the compounds does not interfere with the active binding sites. The result is a conjugate that is both bioactive and site-specific.

The conditions of interfacial condensation of the present invention physically prevent the conjugation reaction from occurring in or near the active binding sites of the antibody. Other chemically reactive groups can participate in the conjugation reaction; while the groups in or near the active binding site are protected. With the immiscible phases for the bioactive compound and the site-specific compound, the droplet or particle size and surface tension are controllable to form the immiscible structures containing the reactive bioactive compounds, such as drugs. As previously discussed, these are physically distanced from the vicinity of any active groups within the active binding site and these active groups are protected from reacting. For example, an immiscible organic phase containing the activated drug could be dispersed in an aqueous phase containing the antibody; this would be optimized so that the size of the organic droplets would be small enough to remain dispersed, yet too large to penetrate into the active binding site of the antibody. The dispersed organic droplets would then be the bulk phase in respect to the activated drug while the continuous aqueous phase would be the bulk phase in respect to the antibody.

In addition, the surface tension present at the interface must be great enough to achieve the desired physical blockage of the region of the active binding sites but not so great as to denature the antibody or other protein.

Alternatively, the activated drug can be dispersed in the aqueous antibody solution as particles of such a size that they will remain dispersed, yet be large enough that they will not be physically able to penetrate the binding site of the antibody or other protein. The particles should be very fine; dispersion with vigorous stirring is used if the particles or crystals have coarse sizes. The particle size will generally be greater than about 10 Angstroms, preferably greather than about 15 Angstroms, ranging up to the limits of dispersability, preferable up to about colloidal size.

The difficulty of providing covalent bonds in conjugates which can be controllably hydrolyzed under physiological conditions has been a substantial problem in the preparation of conjugates in most efforts to date. The problem of partial lability (hydrolysis) of conjugates prepared by prior art methods arises partly from the side reactions which occur during preparation of the conjugates. These side reactions yield a mixture of conjugates which cleave under a variety of conditions that are not controllable in a therapeutic or diagnostic sense. These conjugates are not homogeneous. Those side reactions cause the bioactive compounds to be prematurely cleaved, producing systemic effects, rather than being cleaved at the intended reactive site associated with the binding of the antibody. On the other hand, those which are too low in lability are likely to be inactive or of limited activity, so that both the drug and the antibody are wasted, even if the particular active binding site was in fact protected during conjugation.

The present novel approach for the formation of bioactive, site-specific conjugates employs two or more immiscible phases in the system which allows each reactant to be contained in a phase which is a favorable environment for that reactant while preferentially exposing only the desired reactive groups to condensation reaction conditions at the interface. Therefore, there is generally only one route of reaction, forming only one product. The end result is a very clean chemical reaction of very high specificity with a very homogeneous conjugate product.

The biphasic nature of the interfacial condensation reaction allows for the choice of reaction conditions tailored to the desired reactants and products. In a liquid organic phase-aqueous phase system for example, the hydrophobic groups on the reactant dissolved in the aqueous phase orient the reactant in such a way that they are found at the interface in or near the organic phase. Conversely, the hydrophilic groups on the reactant dissolved in the organic phase orient that reactant in such a way that they are found at the interface in or near the aqueous phase. These groups are then in position to react together to form the desired conjugate. By carefully controlling the various solvents, reactants, activating agents or linkers, if any, and other reaction conditions, specific groups can be consistently positioned to react and homogeneous conjugation product should result.

The specific system can be chosen to allow the drug, or other bioactive compound, to be activated in one phase, the organic, for example, while the antibody remains in the aqueous phase. The stoichiometry of the activating agent can be carefully controlled, since it is not being deactivated by water, and hence side reactions and inactivations of drug and antibody are eliminated. The system can be further refined in other applications to present the desired reactive groups for reaction at the interface between the immiscible phases. For example, in the liquid organic phase-aqueous phase system, amino groups will preferentially react at the interface over the other groups in the molecule. Reactions can therefore be directed preferentially at the amino groups.

It is often preferable to activate one or the other of the reactants, frequently the bioactive compound, prior to undergoing the condensation reaction. In general terms, activation of the bioactive compound, for example, refers to the generation of a specific reactive site, through the formation of an intermediate species, which is highly reactive with the reactive site on the antibody or other protein, e.g., a species which is highly reactive with the amine groups of the antibody and which is not reactive with any other available reactive site in the organic phase. Because under the conditions of interfacial condensation of this invention, the potential reactive sites in the active binding site are physically protected from reacting along with the other potential reactive sites on the protein molecule, the covalent bonding of the condensation reaction is between these other reactive sites in the protein and those of the bioactive compound-intermediate. And, by virtue of the conditions of this invention, this reaction is the only one that will proceed. The intermediate species of the bioactive compound may be formed through the action of a catalyst or through reaction with a linking compound which has a more appropriate reactive site than does the bioactive compound or through activating modification of a particular functional group on the bioactive compound, e.g., ionization or the like, or other techniques of condensation reactions generally. The intermediate of the bioactive compound may also contain cleavable groups that are labile under physiological conditions which would allow for the release of the compound at the target site in the host organism. These linker and cleavable group linkers are described at length in Goers et al., cited previously.

A great variety of compounds are available to form the activating or linking groups on either the antibody or other biologically site-specific compounds or on drugs or other bioactive compounds. When an activation or linking step is used, it is selected to assure optimal conditions for the subsequent intended conjugation reaction. Each of these activating or linking compounds has specific characteristics and thus the reaction conditions for each must be tailored to meet specific demands for optimum reaction efficiency and specificity.

Another advantage of the interfacial condensation process according to this invention for the preparation of the bioactive, site-specific conjugates is that there is greater control over the reaction conditions for each of the reacting compounds. For example, one or more of the reactants can be added incrementally during the reaction. The control of the reaction conditions will materially reduce, and can substantially eliminate, the side reactions and formation of by-products which at best reduce the yields of the conjugate and at worst destroy the site-specificity of the conjugate. It can be seen that this higher selectivity of the process results in easier purification of the reaction products as well as increasing the yield based on the amount of monoclonal antibody used in the reaction. This is in contrast to the traditional conjugation reaction systems which are limited to attempts to provide an environment whose conditions can only be the best possible average for all components with the result that stoichiometries and concentrations of all components must be selected and maintained to avoid degradation of the most sensitive or labile compound that is anywhere in the system. The high concentrations of the individual compounds cause more side reactions and denaturation of sensitive drugs, antibodies or other proteins, and bioreactive molecules.

With the multiple, immiscible phases used to prepare the conjugates by the interfacial condensation reactions of the present invention, each separate bulk phase provides a chemical environment in which the conditions can be optimized for the individual needs of the reactant that is in that phase. The solvents for the one bulk phase are chosen independently of the solvents for the other phases. Therefore, the solvents are chosen to assure the stability of the molecules that will be in that particular phase. When it is desired to also conduct a linking or activation reaction in a bulk phase, the concentrations can be accurately adjusted for optimum stoichiometry of the reactants in that phase by reason of the fact that conjugation at the condensation interface will inherently provide correct orientation of the bioactive compound and the site-specific compound and this will not be a critical rate limiting step in the conjugation reaction. In addition, side reactions are eliminated since the system is designed to allow only the group of choice to be exposed for the conjugation reaction at the interface. The reaction can be carried as close as possible to completion and maximum yield of the bioactive, site-specific conjugate by the driving force of the reaction products leaving the interface and providing more surface ares in which the remaining reactants can react. The kinetics of interfacial condensation are very fast in comparison to solution kinetics so conjugation proceeds rapidly. The conjugate components are not denatured by having to suffer exposure to high concentrations of active reagents so the end products have higher specific activity and fewer side reactions and side effects. The activated intermediate can also be stored in its organic solvent without loss of activity due to hydrolysis.

The need to use an aqueous solution reaction system in traditional methods precludes the attachment of many strongly lipophilic bioactive compounds to antibodies or other targeting proteins. This is a drastic limitation in that the therapeutic compounds of most interest, e.g. drugs, are by their therapeutic nature also very lipophilic, soluble in the fatty regions of cellular material and insoluble in the aqueous regions. The present invention optimizes the solvent conditions for each component of the reaction and they interact only at the interface of the two phases. Therefore, the hydrophilic and lipophilic molecules each remain in solution in their respective phases until participating in the reaction; the parameters of the reaction are adjusted so that each of the reacting molecules can present the proper reactive group at the interface. The result is that the proper application of this invention should allow the preparation of bioactive, site-specific conjugates by conjugation of almost any bioactive compound with any site-specific compound, regardless of their respective physio-chemical properties.

In effecting the interfacial condensation reaction while protecting the active binding site from the reaction, various parameters must be addressed to achieve the specific conditions that are required for a successful conjugation reaction between particular compounds. In general the parameters are as follows:

(1) The molecular weights of the compounds in the reaction and their various solubilities are an important aspect of reaction design. It is fundamental to the intended specificity that the reactants remain in their original phases, so that the protein must not be soluble to any significant degree in the organic phase, and the bioactive compound and its activated intermediate must be preferentially soluble in the organic phase. If solution viscosity is too high, low molecular mobility may be the limiting characteristic of the reaction rate.

(2) The viscosity of each of the phases plays an important role in establishing the rate of interchange of molecules at the interfacial region of the system. Reaction kinetics can be directly affected by a lack of molecular mobility in either phase. As noted above, high solution viscosity can result in low molecular mobility which in turn becomes the rate limiting step.

(3) The partition potential, or miscibility, of the two phases must be controlled to prevent the specificity of the reaction being lost. In addition, if the separate phases become miscible, the protection of the antibody binding site will be compromised or lost.

(4) The interfacial tension must have an intermediate value. It will be somewhere within the limits set by the need to prevent the conjugation reaction from occurring at the active binding site of the site-specific compound being used as the targeting molecule, but not so great as to denature it. The interfacial tension needs to be high enough to prevent the remote phase from wetting the protein molecules so that the reactive component in the remote phase will be physically excluded from the regions of the active binding sites. On the other hand, the interfacial tension should not be so great that the desired reactive sites on the respective compounds cannot become available for conjugation with each other at the interface. Interfacial tension modifiers, generally surface active agents, can be added to the system to adjust the interfacial tension.

(5) The concentration ratio of the reactants is important to consider so that an excess of one will be present to drive the reaction to completion. In general a substantial excess of the bioactive compound will be employed, since the monoclonal antibodies are usually very expensive and difficult to obtain. Further, the ultimate ratio of bioactive compound to the site-specific compound in the conjugate will be selected for a degree of reaction that will tend to maximize the concentration of the bioactive compound but below that which will lower the site specificity of or denature the site-specific compound.

(6) The concentration of reactants in absolute terms can affect the reaction rates and also the maintenance of the phases in the system. It is desirable to remove the reaction products from the interface to increase the chemical driving force on the reactants. For rapid transport of the reaction products away from the interface, it is preferable, when possible, to select the solvent formulations so that the reaction products have a low affinity for the interface or for the organic phase so that the products will move away from the interface and the reaction will be enhanced by the added availability of free interface surface.

As a general rule, the protein, a typical biologically site-specific compound, will be dissolved in an aqueous solution in a convenient concentration for the maintenance of a stable solution. Higher molecular weights require less concentrated solutions, both to avoid precipitation of the protein and to afford viscosities which provide adequate mobility of the molecules at the interface to expose the reactive groups to the interface and to the reaction.

The protein solution may contain other ingredients, but in the most preferred reactions, those of the amine groups, the reaction takes place on the organic phase side of the interface, so that inclusions in the aqueous phase are not active and direct participants in the reaction. It may be desirable to include cosolvents for the conjugate as an aid in the withdrawal of the conjugate product from the interface.

It is desirable to have the bioactive compound as a finely divided disperse phase in the reaction system. This can be in the form of a finely divided solid or droplets of an organic liquid phase. When the liquid organic phase is at saturation with respect to the bioactive compound, upon mixing with the aqueous solution of site-specific compound, a finely divided solid precipitate of the bioactive compound often forms. This precipitate is immiscible with the aqueous phase and is of such a size that the particles of precipitate have the necessary radius of curvature to protect the active binding site from the reaction. The bioactive compound or its activated species are dissolved in an organic phase, usually an organic solvent. The amount of compound is preferably in excess of the amount required for the condensation. The solvent must be to a large extent immiscible with water and must not be a strong solvent for the protein, to prevent intrusion of the reactive species into the aqueous system. At the same time, the solvent must have an affinity for the amine groups of the protein, such that the amine will penetrate the interface and make itself available for reaction. It is also important that the organic phase solvent have low affinity for the conjugate. If the conjugate is more freely soluble in the organic phase than in the aqueous phase, denaturation of the protein, and particularly exposure of the binding site to the reaction system could occur. Indeed, it is preferred that the product be relatively insoluble in the organic solvent. It is also helpful if the organic solvent has limited or low affinity for the available functional groups of the conjugate, so that the interface is cleared of reacted species leaving free surface area for access by unreacted amine groups.

Appropriate organic solvents to meet the relevant criteria are quite numerous. There are extensive published data to enable the choice of appropriate solvents on the basis of these criteria from among the solvents for the bioactive compound or the bioactive compound as modified by activators or linking agents.

It has already been noted that the reaction rates of the interfacial condensation reactions at the interface to prepare the bioactive, site-specific conjugates of the invention are extremely rapid. The overall reaction will depend upon the reaction rate and the surface area of the interface available for reaction as well as the transport and the adsorption and desorption of the reactants and the products. In this context, it is therefore important to note that for the reaction to proceed to high degree of completion that the protein molecules have considerable mobility in the solvent of their phase and that there be available surface area at the interface for the available amine groups on the protein to participate in the reaction. The greater the surface area, the more rapidly the reaction will be able to proceed. High surface area is normally attained by creating a finely-divided immiscible organic phase of the bioactive compound which is dispersed in a continuous aqueous phase containing the protein. The converse would be less commonly utilized. Another approach is to have the phases in large contiguous layers. In both cases, it is important to prevent the immiscible organic phase from penetrating the aqueous phase and reacting with the active binding sites of the protein. The movement of the protein within the aqueous phase and the control of the size and movement of the dispersed organic phase can be enhanced by vigorous stirring; dispersion stabilizers and surface active agents can also be used. It can be seen that an advantage of the having the bioactive compound as an immiscible solid phase is that in this form that it effects both the interfacial condensation and protection of the active binding site.

Conditions for carrying out particular reactions can be modified to obtain optimum results. The system may be heated or cooled, catalysts can be employed and reaction times can be varied. The reactions may be performed by mixing the reactants at once or one reactant may be added incrementally or each may be added continuously. It is important in such cases to avoid conditions which denature the reactants. Monoclonal antibodies, for example, are sensitive to denaturation. By virtue of the nature of the reactions involved, heating is not often required to achieve rapid reaction rates. When it is desired to catalyze the condensation reaction for the conjugation, it is generally necessary to employ catalyst species which are soluble and active in the organic phase, and which are not deactivated by the aqueous component.

In general terms, in forming the bioactive, site-specific conjugate through a condensation reaction to create the covalent bonding between the bioactive compound and the biologically site-specific compound, there is a particular category of condensation reaction of very great interest. As has been noted, the condensation between the amine groups, generally lysine amine groups, of the site-specific compound and appropriate reactive groups of the bioactive compounds is generally preferred by virtue of the facility and flexibility of the various amine condensations that can be used to advantage in the processes of the present invention. Lysine amines can participate in a wide diversity of condensation reactions, with a wide diversity of reactive species. These amine condensations offer a high degree of choice in activation intermediates, linker intermediates, bioactive compounds and a wide range of properties in vivo to suit the requirements for covalent bonding with a particular bioactive compound.

The lysine amine groups may be desirably reacted to form amide, urethane, urea, and thiourea linkages for the covalent moieties in the conjugate. It is also possible to employ the same category of reactions, as well as the condensation with maleimides, to produce thioether linkages through reaction of the cysteine sulfhydryl groups of the site-specific compound, typically a protein molecule, or with the phenolic groups of tyrosine. Through the use of acylating agents it is also possible to react hydroxyl groups on the site-specific compound to form ester linkages.

There are a number of well studied reactive species which can be condensed with lysine amines to form the covalent bond in the conjugate. For example, the amides can be formed by direct condensation with carboxylic acid, or through condensation with mixed anhydrides, and the like. Urethanes are most conveniently formed from condensation with chloroformates, while the ureas and thioureas are generally formed by condensations with isocyanates and thioisocyanates.

Substantially any drug moiety or bioactive compound can be adapted to the present invention by virtue of the presence of one or another of these reactive species or through suitable modification to add such reactive sites as intermediate reaction products. The mole ratio of bioactive compound to site-specific compound in the conjugate will be chosen to maximize the concentration of bioactive compound at the target cell. The ratio can be less than 1 if the conjugate has more than one site-specific compound for each bioactive compound or if the reaction product contains unreacted site-specific compounds as well as the bioactive, site-specific conjugate. There are therapeutic applications in which the combination of conjugate and unreacted site-specific compound can be used. In conventional chemotherapeutics, the molar ratios in the conjugate will generally be in the range of about 3 to about 20.

One of the particular advantages of the present invention resides in the fact that in one class of preferred embodiments the bioactive species for the condensation can be isolated and purified in a protein free system prior to undergoing the condensation reaction. The bioactive compound can be formed and treated with activators or linker molecules, if necessary, to form the reactive species which is then purified. This substantially pure reactant is provided to the reaction system, and because of the nature of the interfacial condensation reactions of the present invention, the formation of side reactions and by-products is substantially eliminated from the system.

The present invention finds particular utility in making it possible to form conjugates of lipophilic bioactive compounds and monoclonal antibodies. Such conjugates have not been available at all, or have exhibited such losses of binding site specificity and/or activity that their utility has been extremely limited. In addition, the present invention has the advantage for substantially all bioactive compounds, and particularly for virtually all classes of cytotoxic agents, of exceptional purity and freedom from side reactions and by-products. As a major advance in drug and diagnostic therapy, it is a central feature of the present invention to make such reactions possible and even facile while providing bioactive conjugates that retain the full measure of selectivity and activity for specific binding sites. Thus the present invention provides an entirely new range of conjugates not available to the art heretofore.

The covalent bonding in the bioactive, site-specific conjugates of this invention can be characterized by two specific types of arrangements: A) direct conjugation of the bioactive compound to the site-specific compound, often involving the formation of an activated intermediate, and B) indirect conjugation of the bioactive compound to the site-specific compound by insertion of an intermediate linker molecule between the two main constituent molecules. In both arrangements, the linkage to the bioactive compound can either be labile under cellular conditions, allowing for the release of the bioactive agent at the target or stable under cellular conditions where the conjugate is per se bioactive. The terms bioactive compound and biologically site-specific compound are intended to include the main constituent molecules as well as the molecules in association with their activators or their linkers as the context indicates.

The covalent bonding of these arrangements uses well established chemistry and is described in more detail in the following illustrations with the understanding that the reactive groups in the active binding site of the site-specific compound are protected from reaction by the principles previously discussed for the practice of the invention. Thus, the reactive groups of the active binding site are excluded from the covalent bonding reaction by the use of interfacial condensation conditions.

Direct Conjugation—the bioactive compound and the site-specific compound are joined by direct covalent bonds to form the conjugate. Direct conjugation can proceed via an activated intermediate. Either the bioactive compound or the site-specific compound can be used to form the activated intermediate. Examples of this conjugation are:

Conjugation through an alcohol group on the bioactive compound—a typical compound would be retinol (Vitamin A). Vitamin A and its derivatives will be abbreviated $V_A$ and show the reactive group, e.g. $V_A$-$CH_2OH$ for retinol. For example, retinol is reacted with cyanogen bromide (CNBr) to form the activated isocyanate intermediate. This activated intermediate then condenses with the amino terminus of lysine residues on the antibody (Ab). The result is the formation of an isourea linkage, which is at least partially labile under cellular conditions, so the retinol can be cleaved from the antibody upon internalization by the cell. Another example of this type of linkage is the activation of retinol with tosyl chloride resulting in an amide linkage to the antibody when the intermediate is reacted with the amino terminus of the antibody lysine residues.

Retinol may also be reacted with a carbodiimide, either water or organic soluble, to form an activated intermediate. The activated intermediate then reacts with the amino terminus of lysine residues on the antibody. The result is the formation of a urethane linkage which will not be cleaved upon internalization by the cell. Other activating compounds which are useful in making direct, non-labile linkages from alcohol derivatives of retinoids and carotenoids are azo compounds and $NaIO_4$-$NaBH_4$.

Conjugation through a carboxylic acid group on the bioactive compound—a typical compound would be retinoic acid ($V_A$-COOH). In this case direct condensation is possible. The resulting amide linkage would be slightly labile under cellular conditions, but such direct covalent bonding is generally of greatest interest when the conjugate is per se bioactive without cleavage.

Retinoic acid may be reacted with a carbodiimide to form an activated intermediate. Upon reaction with the amino terminus of lysine residues on the antibody, an amide linkage would be formed, which is not labile under cellular conditions. Other activating compounds which are useful in making direct, non-acid-labile linkages from carboxylic acid derivatives of retinoids and carotenoids are 1ethoxycarbonyl-2-ethoxy-1,2 dihydroquinoline, (EEDQ) and N-hydroxysuccinimide (NHS).

Indirect Conjugation with Intermediate Linker Molecules—for these covalent bonding arrangements, either the bioactive compound or the site-specific compound can be associated with the linker molecule. The linker molecule can be treated with an activator to form an activated linker intermediate prior to undergoing the final conjugation reaction. The bioactive/linker molecule can be any compound of the formula

A—L—CO—X, where L is any aliphatic or aromatic group or a peptide chain linked to a bioactive compound A, and X may be: halogen; —O—NR—, amino ester; —O—CO—R, including mixed anhydrides and symmetrical anhydrides (where X=R); isocyanate; thioisocyanate; maleimides; or benzyl groups (e.g., orthodiketones). Depending on the intended reactive site on a site-specific compound, typically a protein, these reactive linkers result, variously, in amide, ester, urea, ether, polyurethane, thiourea, and thioether linkages. The linkage between A and L is desirably adapted to be labile under the conditions in the cell of the host organism if the conjugate is not per se bioactive. Many such linkages are known in the art, and substantially any of those suited to the target site in the host organism may be employed. The particular advantage of the present invention resides in the fact that the conjugate will be exceptionally pure, and not contaminated by side reaction by-products, so that the conjugate will be free of components and constituents which result in random breakdown or lysis anywhere in a person or other host organism.

Typical examples of these indirect conjugations are:

Conjugation through an alcohol group of a bioactive compound, for example, retinol. Retinol is initially reacted with a linker molecule, such as aconitic anhydride. This results in the formation of an ester linkage which is labile and may later be cleaved upon internalization by the cell. The acid group of the linker molecule is then activated with NHS and reacted with the amino terminus of lysine residues on the antibody.

An alternative approach, for a linkage with the same properties, is to use an azo compound for the linker, activate with sodium nitrite in hydrochloric acid, and react with the aromatic ring of a phenol derivative of the antibody. Other linker molecule-activating compound combinations which are useful in making indirect, labile linkages from alcohol derivatives of retinoids and carotenoids are any unsaturated triacid anhydride, triacid, or acid chloride.

Retinol may also be reacted with a linker molecule, such as epichlorohydrin. The epoxide group on the linker molecule is then reacted with the amino terminus of lysine residues of the antibody resulting in a hydroxyamine linkage which is not labile under cellular conditions. An alternative approach to formation of the same type of linkage is to first convert the retinoid from an alcohol to an aldehyde with $NaIO_4$. This procedure would thus apply for any aldehyde derivative of a bioactive compound. Retinal, for example, is then reacted with a linker molecule of the form $NH_2$—R—COOH, where R is any aliphatic or aromatic group. The intermediate is activated with EEDQ and reacted with the amino terminus of lysine residues of the antibody. The amide covalent bond of the conjugate would not be labile under cellular conditions. Other linker molecule and activating compound pairs which are useful in making indirect, non-labile linkages from alcohol derivatives of retinoids and carotenoids are benzoquinone and trichlorotriazine.

Conjugation through a carboxylic acid group of a bioactive compound, for example, retinoic acid. A linker molecule, such as an amino anhydride, would be reacted with retinoic acid and EEDQ. This would form a linker intermediate containing an acid amide linkage which is labile under cellular conditions. The linker intermediate would then be subsequently reacted with the amino terminus of lysine residues of the antibody.

Retinoic acid may also be reacted with a linker molecule of the form HO—R—OH, where R is any aliphatic or aromatic group. This results in an ester linkage which is not generally labile under cellular conditions. The linker intermediate is then activated with a carbodiimide and then reacted with the amino terminus of lysine residues of the antibody forming a urethane linkage in the conjugate.

Conjugation by use of a disulfide bond—a typical retinoid is retinol. Retinol is first converted to a mercaptol. This is then reacted with a reduced form of the antibody to link the two molecules by a disulfide bond and form the conjugate.

A preferred group of covalent bonds in the conjugates are formed through one or more C, N, O and S atoms. These may be monovalent or polyvalent bonds. Generally, these bonds are in the form of one or more amide, acid-amide, cyano, hydrazido, hydrazidino, polysulfide, ester, ether, hydroxy-amine, isourea, thioether, thiourea, urea and urethane linkages. The corresponding reactive groups of the parent bioactive and site-specific compounds are as described above.

The application of particular combinations of the above techniques for the preparation of bioactive, site specific conjugates is exemplified in the following illustrative examples, which should be construed as illustrative and not as limiting the scope of the present invention. The illustrations of the monoclonal antibodies $KS_{1/4}$ and 9.2.27, which are known in the art, are to demonstrate a class of antibodies that are site-specific for solid human cancer tumor antigens; these tumors are resistant to conventional chemotherapy.

EXAMPLE 1

One milligram of cis-retinoic acid was dissolved in 100 μl of N-methyl pyrrolidone, NMP. One milligram of N-hydroxy succinimide, NHS, was added and the mixture was allowed to react for 5 minutes. Next, one milligram of dimethyl aminopropyl ethyl carbodiimide, EDCI, was added, and the resulting clear yellow solution was allowed to react for 1 hour at room temperature, followed by 2 hours at 4° C. The solid succinimic ester intermediate was formed.

The suspension of solid intermediate was added in excess mole ratio to an aqueous solution of a monoclonal antibody, designated 9.2.27, having a concentration of 10 mg/ml. The mixture was initially a very cloudy suspension due to the presence of the solid precipitate of retinoic acid-ester intermediate in very finely divided form. With vigorous mixing of the solid and aqueous phases to promote the interfacial condensation reaction, the mixture gradually cleared as the reaction progressed until there was a residual, slightly cloudy suspension of solid succinimic intermediate precipitate. The suspension was centrifuged to recover the aqueous phase which contained the conjugate. The product conjugate was purified by gel chromatography.

On analysis, the product was found to be a conjugate of 3 molecules of the retinoic acid per molecule of the antibody. The conjugate showed substantially the same binding activity and specificity as the original monoclonal antibody.

This Example also illustrates the use of a solid-liquid interface during the interfacial condensation between the bioactive compound and the site-specific compound.

EXAMPLE 2

Trans-retinoic acid was dissolved in dioxane, at a level of 18.5 mg ($6.1 \times 10^{-5}$ moles) in 1 ml. Then 16.8 mg of carbonyl diimidazole ($10 \times 10^{-5}$ moles) was added to the solution with rapid stirring while protected from the light. The N-substituted carbamate was formed.

A second solution was formed of 10 mg per ml of a monoclonal antibody, designated 9.2.27, in a phosphate buffer, and the pH was raised to 8.3. The retinoic acid carbamate solution was at saturation and was added in two increments. First, a 100 μl portion of the N-retinoic acid carbamate solution was added. It was shaken vigorously to form the finely divided suspension of the retinoic carbamate solution in the aqueous solution of antibody. This proceeded to react. Later, a second 100 μl portion of the retinoic acid carbamate solution was added with vigorous shaking to maintain the suspension while the reaction continued.

After about ten minutes, the suspension was centrifuged, and the aqueous fraction containing the conjugate was purified by diafiltration. The retinoic acid to antibody mole ratio was 8:1. The conjugate showed substantially the same binding activity and specificity as the original monoclonal antibody.

EXAMPLE 3

Methotrexate was reacted with N-hydroxy succinimide in a 1:1 mole ratio to give a solid succinimic ester of the Methotrexate in the form of a very fine dispersion of the solid precipitate in water. This intermediate is insoluble in water.

A monoclonal antibody solution, 10 ml, containing 5 mg protein per ml, of an antibody designated $KS_{1/4}$, was stirred cold while a 305 μl portion of the aqueous suspension of the solid succinimic methotrexate ester, containing 5 mg/ml, was added dropwise. On the addition of each drop, the solid precipitate formed a cloudy suspension which gradually cleared as the reaction proceeded. After addition of the total of the intermediate, a clear solution of the conjugate was obtained which was diafiltered using 0.9% saline. The resulting conjugate had a mole ratio of methotrexate to monoclonal antibody of 12:1. The conjugate showed substantially the same binding activity and specificity as the original monoclonal antibody.

This Example also illustrates the use of a solid-liquid interface during the interfacial condensation between the bioactive compound and the site-specific compound.

EXAMPLE 4

An aqueous solution of $KS_{\frac{1}{4}}$ monoclonal antibody was prepared. The antibody was IgG1 and IgG2, purified with protein A, $OD_{280} = 3.15$. The pH of the solution was adjusted to 6.8.

A solution of Methotrexate-N-hydroxy succinimide ester (MTX-NHS) was prepared in dimethylacetate (DMAc). As this solution was added dropwise to the aqueous solution of antibody, a finely divided precipitate was formed and was suspended in the aqueous phase. The addition occurred over a period of two minutes, the pH decreased to 6.0 and was increased to 6.6. A 17 mole ratio excess of MTX-NHS was used. After the addition was completed, the reaction mixture was stirred for an additional hour; then, the product conjugate was recovered from its aqueous solution by dialysis, concentration and sterile filtration. The ratio of MTX to $KS_{\frac{1}{4}}$ was about 7:1 and the conjugate had substantially the same site-specificity as the antibody itself.

EXAMPLE 5

The procedure of Example 4 was repeated on a 100-fold scale up and using larger amounts of MTX-NHS. The mole ratio of reactants was 18:1. The conjugate had a ratio of MTX to antibody of 10 and it had substantially the same site-specificity as the original antibody.

EXAMPLE 6

(a) Methotrexate was reacted with carbonyldiimidazole to form the carbonyl imidizole derivative of Methotrexate. This was dissolved in DMAc.

An aqueous solution of $KS_{\frac{1}{4}}$ (m.w., approx 160,000) was prepared. The Methotrexate imidizole solution was added to the solution of monoclonal antibody at a molar excess of 17:1. It formed a liquid/liquid suspension in the aqueous phase. The pH was adjusted to 7.8 with aqueous NaOH while the reaction proceeded for one hour. No visible solid precipitate was observed. The conjugate was recovered from the aqueous solution and purified by column chromatography; it had a ratio of MTX-$KS_{184}$ of 6:1.

(b) The reaction run of (a) was repeated using increased amounts of the Methotrexate imidizole solution. This increased the relative volume fraction of the disperse phase. Considerable cloudiness was noted as the reaction proceeded. The conjugate was recovered from the aqueous solution and purified by column chromatography.

(c) The reaction run of (a) was repeated by using dropwise addition of the Methotrexate imidizole over a period of two minutes. As each drop was added to the aqueous solution, a solid, finely divided precipitate was formed. The mole ratio of reactants was 19:1, Methotrexate to monoclonal antibody. After addition was completed, the reaction was continued for one hour. The conjugate was recovered from its aqueous solution by filtration and diafiltration. The conjugate was identified by UV spectroscopy.

EXAMPLE 7

(a) Doxorubicin (DXR) was dissolved in a mixture of DMAc and dioxane. This was reacted with diethylenetriamine pentaacetic anhydride (DTPA). 0.5 ml of this solution was slowly added to 3 ml of an aqueous solution of monoclonal antibody designated as 9.2.27 (4 mg/ml). The reaction was continued with stirring for one hour. The conjugate was recovered; its UV spectrum indicated a low degree of covalent bonding between DXR and 9.2.27.

(b) The above reaction was repeated with the addition of carbodiimide to the mixture of monoclonal antibody and DXR adduct. The conjugate was recovered and it had substantially the site specificity of the original antibody.

EXAMPLE 8

Vinblastin was reacted with carbonyldiimidazole in dioxane for ten minutes. This solution was added to an aqueous solution of monoclonal antibody, 9.2.27. A cloudy suspension formed when the solutions were mixed; this was a liquid/liquid suspension. The conjugate was recovered from its aqueous solution and purified in a NAP-5 column. The conjugate had substantially the same site-specificity as the original antibody.

EXAMPLE 9

(a) A solution of retinoic acid in chloroform was added to an aqueous solution of monoclonal antibody, 9.2.27. The mole ratio of reactants was 166:1. On mixing, the chloroform solution became a finely divided disperse phase in the continuous aqueous phase, the mixture was cloudy. The reaction proceeded for three hours at room temperature. The conjugate was recovered from its aqueous solution by column filtration. Covalent bonding between the antibody and the acid was determined by UV spectroscopy.

(b) Retinoic acid was dissolved in dioxane. It was reacted with carbonyl diimidazole to form the imide derivative of the acid.

This solution was reacted with an aqueous solution of monoclonal antibody, 9.2.27, pH 8.3, in two steps. One-third of the imide was added and the mixture was shaken to form a suspension. Similarly, the remaining two-thirds was added and the reaction continued for thirty minutes. The conjugate was recovered from its aqueous solution by diafiltration through a 10 micron membrane. This conjugate had a mole ratio of retinoic acid to antibody of 10:1 and it had substantially the same site specificity as the original antibody.

(c) Retinoic acid was dissolved in dry chloroform and reacted with carbonyldiimidazole to form the imide. This was a clear, deep yellow solution which was added to an aqueous phosphate buffered saline solution of monoclonal antibody, 9.2.27. On mixing, it formed a cloudy suspension. The reaction proceeded at room temperature for one hour while being stirred; then, the reaction temperature was lowered to 4/C with continual stirring. The conjugate was recovered by p-10 gel chromatography; it had retinoic acid covalently bound to antibody at a mole ratio of 12:1.

(d) Retinoic acid was suspended in mineral oil which was then mixed with methylene dichloride to form a yellow solution. Carbonyl diimidazole was added and reacted to form the imide of the acid. A suspension was formed by adding this mixture to an aqueous solution of monoclonal antibody, 9.2.27, in PBS, pH 8.2. After the reaction was complete, the conjugate was recovered from its aqueous solution by gel chromatography.

EXAMPLE 10

Retinoic acid was reacted with a mixture of N-hydroxy succinimide and ethylene carbodiimide in a solvent of DMAc and N-methyl pyrrolidone. The reaction was at room temperature for one hour and at 4/C for four hours. A clear yellow solution was obtained.

An aqueous solution of monoclonal antibody, 9.2.27, was diafiltered against PBS. The clear yellow solution of therapeutic compound was diluted 9:1 with DMAc and added dropwise to the 9.2.27 solution with stirring. Each drop formed a solid/liquid suspension in the aqueous media. After the reaction was completed, the conjugate was recovered from its aqueous solution by diafiltration. The retentate held the conjugate and the covalent bonding was determined by UV spectroscopy.

EXAMPLE 11

Methotrexate was reacted with adipic hydrazide to form the mono-hydrazidinyl derivative CN-MTX—(C-H$_2$OH)—C=N—NH—CO—(CH$_2$)$_4$—CONHNH$_2$. This was prepared by dissolving 6.5 mg ($10^{-5}$ mol) of the Methotrexate in 100 microliters of DMAc. Then, 15 mg of adipic hydrazide in 100 microliters of DMAc/LiCl complex was added to the solution. This was acidified by the addition of 3 microliters of acetic acid. The reaction continued with stirring for 18 hours. The product was a brownish cloudy solution which was filtered through a silica gel plug with MeOH as an eluent. The bioactive compound was in the filtrate which was a red solution. This was concentrated to about 350 microliters. The reaction effluent was analyzed by TLC (19:1 CHCL$_3$/MeOH); this indicated that the starting materials had been fully reacted. It is advantageous to have the bioactive compound at or near or above saturation in its solution so that the formation of the liquid/liquid or solid/liquid suspension is facilitated. Methotrexate and its derivatives are examples of compounds that readily form saturated and supersaturated solutions which, as discussed above, can be used to participate in the interfacial condensation reaction process.

The site-specific compound was an oxidized carbohydrate adduct of KS$_1$. It was prepared by oxidation with sodium periodate of the terminal glucose group in the carbohydrate to the dialdehyde form.

The solution of bioactive compound was added to an aqueous solution of the site-specific compound. Upon addition, it formed a fine solid precipitate in the aqueous media. The molar ratio of bioactive compound to site-specific compound was about 40:1. The pH dropped from 5.6 to 5.2 and the reaction was continued overnight at 2/C. There was a clear red solution containing the immunoconjugate, indicating the addition of the hydrazide group in the bioactive compound to the aldehyde group of the site-specific compound and the formation of the site-specific, bioactive immunoconjugate by hydrazinidyl bonds.

EXAMPLE 12

Three linkers are synthesized by reacting either L-alanyl-L-alanyl-L-alanine methyl ester acetate, L-alanyl-L-leucinyl-L-alanyl-L-leucine methyl ester acetate, or L-leucinyl-L-alanyl-L-leucinyl-L-alanine methyl ester acetate with maleic anhydride using DMAc as the solvent and Et$_3$N as a base. A FT-IR as well as high field 300 Mhz NMR spectra are in keeping with the assigned structure

```
         HO—CO—CH=CH—CO—NH—peptide—COOMe.
Peptide = —L—Ala—L—Ala—L—Ala—   (AAA)
          —L—Ala—L—Leu—L—Ala—L—Leu—  (ALAL)
          —L—Leu—L—Ala—L—Leu—L—Ala—  (LALA)
```

Any of the linkers is converted to the acid chloride with the intention of reacting it with the primary alcohol at C-14 of morpholino doxorubicin (M-DXR) and cyanomorpholino doxorubicin (CM-DXR) to give the corresponding esters. The terminal methyl ester functionality of the linkers may then be converted to a suitable group compatible to linking of an antibody resulting, for example, in a conjugate having the structure (C)M—DXR—CO—CH=CH—CO—NH-peptide-
CO—NH-Antibody.

EXAMPLE 13

Any of the linkers from Example 12 is treated with hydrazine hydrate in either MeOH or DMAc as the solvent to give linkers having the structure HO—CO—CH=CH—CO—NH-peptide-CONH—NH$_2$.

The acid hydrazide obtained may be made to react with the carbonyl group at C-13 of morpholino doxorubicin as well as cyanomorpholino doxorubicin to give the corresponding hydrazides having the structure (C)M—DXR=N—NH—CO-peptide-
NH—CO—CH=CH—COOH.

The acid group of the linkers may then be converted to the N-hydroxy succinimide derivatives.

These compounds are now able to react with the ε-amino groups on the lysines of the antibody to give the desired drug-linker-antibody conjugates.

The products of the process of this invention are improved in comparison to the prior art materials in several respects. When the reaction has been completed, the conjugates have a significantly higher site-specificity in respect to approaching the site-specificity of the original antibody. The materials in the reaction effluent contain a higher proportion of the desired conjugate and fewer byproducts and side reactants. With a reaction product having its site-specific conjugate at this degree of cleanliness, it substantially reduces purification steps because as a result of the reaction conditions essentially all of the bioactive high molecular weight components are the desired site-specific conjugates and not the denatured conjugates. With such homogeneous conjugates, the purification can be done on the basis of removing undesirable low molecular components, e.g. unreacted bioactive compounds. Therefore, the unwanted materials can be removed by dialysis and filtration and the like. The thus processed reaction products are then in a useful therapeutic form and can also be further purified if desired. While in some cases the individual conjugate will be the objective, these products do not necessarily need to be isolated into the individual species of bioactive, site-specific conjugates.

The principles of this invention are applicable to bioactive compounds and site-specific compounds generally. The use of interfacial condensation and the variations described above gives very pure yields of the bioactive, site-specific conjugates. In addition, these processes make products that include new compounds. The invention is intended to cover these and equivalent variations as would be generally practiced in the field to which it applies.

What is claimed is:

1. A method for the preparation of a conjugates of therapeutic compounds and biologically site-specific compounds, wherein each of said biologically site-specific compounds contains at least one active binding site, comprising:

(a) providing an aqueous solution of said biologically site-specific compounds to form an aqueous phase;

(b) providing said therapeutic compounds in a phase immiscible with said aqueous phase and forming an interface therewith;

(c) conducting an interfacial condensation of one or more of said biologically site-specific compounds and one or more of said therapeutic compounds to form one or more covalent chemical bonds between said biologically site-specific compounds and said therapeutic compounds while protecting said active binding sites of said biologically site-specific compounds from the condensation reaction, said interfacial condensation resulting in the formation of biologically site-specific, therapeutic compound conjugates of said compounds; and (d) recovering said biologically site-specific, therapeutic conjugates of said compounds.

2. The method according to claim 1 wherein said biologically site-specific compounds are proteins.

3. The method according to claim 2 wherein said proteins are antibodies or antibody fragments.

4. The method according to claim 2 wherein said proteins are monoclonal antibodies.

5. The method according to claim 2 wherein said proteins are polyclonal antibodies.

6. The method according to claim 1 wherein said therapeutic compound is a member selected from the group consisting of toxins, cytotoxins, cytotoxic and cytoactive agents, alkylating agents, antibiotics, antimetabolites, hormones, neurotransmitters, radioopaque dyes, fluorogenics, bio-markers, photochemicals, cell membrane modifiers, antiproliferatives, and heavy metals.

7. The method according to claim 4 wherein said therapeutic compound is a lipophilic cytotoxin.

8. The method according to claim 4 wherein said therapeutic compound is a member selected from the group consisting of doxorubicin, vinblastin, methotrexate, retinoids, and carotenoids.

9. The method according to claim 4 wherein said therapeutic compound is platinum.

10. The method according to claim 1 wherein step (a) further comprises adding to said site-specific compounds intermediate compounds wherein said intermediate compounds are members selected from the groups consisting of activating, linking, spacing, and cleavable compounds.

11. The method according to claim 10 wherein said intermediate compounds form a part of the chemical bond between said biologically site-specific compounds and said therapeutic compounds.

12. The method according to claim 10 wherein said intermediate compounds are peptide chains.

13. The method according to claim 10 wherein said intermediate compounds are physiologically cleavable compounds.

14. The method according to claim 1 wherein said therapeutic compounds are contained in a liquid phase.

15. The method according to claim 1 wherein said therapeutic compounds are contained in a solid phase.

16. The method according to claim 1 wherein said immiscible phase has a local radius of curvature of at least about 10 Angstroms at the active binding site or sites of the site-specific compounds.

17. The method according to claim 1 wherein said immiscible phase has a local radius of curvature of at least about 20 Angstroms at the active binding site or sites of the site-specific compounds.

18. The method according to claim 1 wherein said immiscible phase has a local radius of curvature from of at least about 10 Angstroms up to about colloidal size at the active binding site or sites of the site-specific compounds.

19. The method according to claim 1 wherein said aqueous phase is a continuous phase.

20. The method according to claim 1 wherein said conjugate has a molar ratio of bioactive compound to site-specific compound greater than 3.

21. The method according to claim 1 wherein said site-specific compound is specific for solid human tumor antigens.

22. A method for the preparation of conjugates of bioactive compounds and biologically site-specific compounds, wherein each of said biologically site-specific compounds contains at least one active binding site, comprising:
(a) providing an aqueous solution of said biologically site-specific compounds to form an aqueous phase;
(b) providing said bioactive compounds in a phase immiscible with said aqueous phase and said immiscible phase having a local radius of curvature of at least about 10 Angstroms at the active binding site or sites of the site-specific compound;
(c) forming an interface therewith;
(d) conducting an interfacial condensation of one or more of said biologically site-specific compounds and one or more of said therapeutic compounds to form one or more covalent chemical bonds between said biologically site-specific compounds and said therapeutic compounds while protecting said active binding sites of said biologically site-specific compounds from the condensation reaction, said interfacial condensation resulting in the formation of biologically site-specific, therapeutic compound conjugates of said compounds; and
(e) recovering said biologically site-specific, therapeutic conjugates of said compounds.

23. The method according to claim 22 wherein said local radius of curvature is at least about 20 Angstroms.

* * * * *